(12) United States Patent
Heni et al.

(10) Patent No.: US 10,537,232 B2
(45) Date of Patent: Jan. 21, 2020

(54) ENDOSCOPE (OR EXOSCOPE) WITH A ROTATABLY ARRANGED ELECTRONIC IMAGE RECORDER

(71) Applicant: Karl Storz SE & Co. KG, Tuttlingen (DE)

(72) Inventors: Andreas Heni, Fridingen (DE); Markus Kupferschmid, Emmingen-Liptingen (DE); Daniel Ulmschneider, Nendingen (DE); Christian Graf, Emmingen-Liptingen (DE); Peter Schwarz, Tuttlingen-Nendingen (DE); Kevin Pilz, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 253 days.

(21) Appl. No.: 14/495,322

(22) Filed: Sep. 24, 2014

(65) Prior Publication Data

US 2015/0085093 A1  Mar. 26, 2015

(30) Foreign Application Priority Data

Sep. 24, 2013 (DE) .................. 10 2013 110 544

(51) Int. Cl.
  *A61B 1/04* (2006.01)
  *A61B 1/012* (2006.01)

(52) U.S. Cl.
  CPC ............ *A61B 1/04* (2013.01); *A61B 1/0125* (2013.01)

(58) Field of Classification Search
  CPC ........................................ A61B 1/04
  USPC ............................................................ 348/65
  See application file for complete search history.

(56) References Cited

U.S. PATENT DOCUMENTS

| | | | | |
|---|---|---|---|---|
| 4,543,960 A | * | 10/1985 | Harui | A61B 8/12 600/462 |
| 5,176,142 A | * | 1/1993 | Mason | A61B 8/12 600/463 |
| 5,305,755 A | * | 4/1994 | Nakao | A61B 8/12 600/444 |

(Continued)

FOREIGN PATENT DOCUMENTS

| | | |
|---|---|---|
| DE | 102009054413 A1 | 5/2011 |
| DE | 102011054031 A1 | 10/2012 |

(Continued)

*Primary Examiner* — Sath V Perungavoor
*Assistant Examiner* — Amir Shahnami
(74) *Attorney, Agent, or Firm* — Whitmyer IP Group LLC (57) ABSTRACT

An endoscope or exoscope having a shaft and at least one objective and at least one electronic image recorder for recording an image of an object field, wherein the objective and image recorder are arranged in a distal end region of the endoscope or exoscope, and includes at least one cable, routed within the endoscope or exoscope, for supply of and/or image transmission from the electronic image recorder, wherein the electronic image recorder includes an optical unit, which is rotatable about a first axis of rotation identical or approximately parallel to a direction of view of the scope, and on which the cable is connected and can be wound on a circumferential surface of the optical unit, and wherein the distal end region includes a cavity, in which storage for holding a section of the cable is held.

13 Claims, 6 Drawing Sheets

(56) References Cited

U.S. PATENT DOCUMENTS

| | | | | |
|---|---|---|---|---|
| 5,353,798 A | * | 10/1994 | Sieben | A61B 8/12 |
| | | | | 128/925 |
| 5,469,852 A | * | 11/1995 | Nakamura | A61B 8/12 |
| | | | | 600/463 |
| 5,562,096 A | * | 10/1996 | Hossack | A61B 8/12 |
| | | | | 600/446 |
| 5,689,365 A | | 11/1997 | Takahashi | |
| 5,771,896 A | * | 6/1998 | Sliwa, Jr. | A61B 8/12 |
| | | | | 600/462 |
| 6,471,653 B1 | * | 10/2002 | Jordfald | A61B 8/12 |
| | | | | 600/462 |
| 2003/0055437 A1 | * | 3/2003 | Yasunaga | A61B 1/00149 |
| | | | | 606/130 |
| 2008/0249418 A1 | * | 10/2008 | Shikata | A61B 8/08 |
| | | | | 600/459 |
| 2012/0123212 A1 | * | 5/2012 | Dahmen | A61B 1/0008 |
| | | | | 600/178 |
| 2013/0121005 A1 | * | 5/2013 | Dahmen | A61B 1/00179 |
| | | | | 362/318 |
| 2013/0182091 A1 | * | 7/2013 | Kohno | A61B 1/00183 |
| | | | | 348/76 |
| 2014/0249369 A1 | * | 9/2014 | Hanabusa | A61B 1/00183 |
| | | | | 600/109 |

FOREIGN PATENT DOCUMENTS

| | | |
|---|---|---|
| DE | 102011121303 A1 | 6/2013 |
| JP | S6084524 A | 5/1985 |
| JP | H10192233 A | 7/1998 |
| WO | 2013051168 A1 | 4/2013 |

\* cited by examiner

ENDOSCOPE (OR EXOSCOPE) WITH A ROTATABLY ARRANGED ELECTRONIC IMAGE RECORDER

FIELD OF THE INVENTION

The present invention relates to an endoscope or an exoscope.

BACKGROUND OF THE INVENTION

These days, endoscopes are used for a multiplicity of applications in medicine and technology. Endoscopes typically comprise a rigid or flexible elongate shaft, which is suitable for insertion into a cavity, and in the distal (i.e. observer-distant) end region of which an objective is arranged for generating an image of an object field in the cavity. In order to record and transmit the endoscopic image from the distal end of the endoscope to the proximal (observer-near) end, provision can be made for an electronic image recorder, e.g. a CCD chip, in the region of the distal end of the shaft and for electric lines within the shaft. The image recorded by the electronic image recorder can be evaluated by an evaluation and display apparatus connectable to the proximal end of the endoscope, depicted on a screen for an observer and/or stored, e.g. for documentation purposes. Since, in general, the observed cavity does not have sufficient amounts of light, a light guidance system is furthermore provided within the shaft in order to transport sufficient amounts of light to the distal end of the endoscope, where it is used for illuminating the cavity.

If an endoscope comprising an objective and an electronic image recorder assigned to said objective in the distal end region of said endoscope is rotated about the longitudinal axis of the shaft, the recorded image depicted on the screen is also rotated in the process. This makes it difficult or impossible for an observer, who may be e.g. the surgeon performing a surgical operation, to orient himself or herself within the cavity. This applies, in particular, if the endoscope comprises a stereo optical system for generating a stereoscopic image, since the stereo basis is also rotated in this case.

JP 10192233 A has disclosed a stereoscopic electronic endoscope comprising an oblique view optical system, wherein provision is made for a motor-driven adjustment of a rotation element, which supports an optical system comprising two objective lens systems which are spaced apart transversely in relation to the optical axis, and two CCD image recorders assigned thereto. The signal cables of the CCD image recorders are routed in a flexible tube in an axial bore of the rotation element. U.S. Pat. No. 5,689,365 has disclosed a stereoscopic endoscope, which comprises a front optical system with a single optical axis and a rear optical system with a plurality of optical axes. Together with two photoelectric image recorders, the rear optical system can be rotated about an axis parallel to the shaft of the endoscope relative to the front optical system. The signal line of the image recorders is routed and twisted in the extension of the axis of rotation of the stereo optical system. The above-described arrangements are not ideal in respect of the durability of the cables.

DE 10 2011 054 031 A1 has disclosed a device for observing and illuminating an object field on a patient from a location away from the body of the patient, comprising an optical system for observing the object field and an illumination apparatus for illuminating the object field. The device furthermore comprises a shaft, at the distal end of which a head part is arranged, which head part is widened compared to the shaft and in which at least one emitting illumination unit for homogeneous illumination of the object field is arranged. Feed lines for the at least one illumination unit extend through the shaft. Furthermore, the elongate shaft can hold an image forwarding apparatus, which forwards the image of the operation field to a proximal end of the shaft. Such a device is also referred to as "exoscope". In particular, such an exoscope enables the illumination and observation of an operation field during a surgical operation from a working distance of e.g. 25 to 75 cm such that the work space of the surgeon remains practically unrestricted by the exoscope. To this end, the exoscope can be affixed on a holder in a suitable position and with a suitable orientation. The aforementioned problem that the image recorded by an electronic image recorder is rotated on the screen, on which it is displayed for an observer, when the exoscope is rotated also arises in the case of an exoscope.

SUMMARY OF THE INVENTION

It is an object of the present invention to specify a generic endoscope or exoscope with a rotatably arranged electronic image recorder and an improved cable routing.

This object is achieved by a device in accordance with the invention.

An endoscope or exoscope according to the invention comprises a shaft, which preferably has an elongate and rigid design, but may also have a very short design, and comprises at least one objective and at least one electronic image recorder for recording an image of an object field, wherein the at least one objective and the at least one electronic image recorder are arranged in a distal end region of the endoscope or exoscope. The distal end region of the endoscope or exoscope can be a distal end section of the shaft, or else a head part, widened compared to the shaft, which is arranged at a distal end of the shaft. Furthermore, the endoscope or exoscope comprises at least one cable for supply of and/or signal transmission from the electronic image recorder or the at least one electronic image recorder, which cable is routed within the endoscope or exoscope. In particular, the cable can be routed within the shaft and extend from a proximal end section of the shaft to a distal end section of the shaft or to a head part arranged at the distal end of the shaft and connected to the at least one electronic image recorder arranged therein. At the proximal end section of the shaft, or else at a handle connected to the proximal end section of the shaft, provision can be made for connectors for facilitating a connection to external supply, evaluation and/or display apparatuses. In particular, the cable serves for the actuation of the at least one electronic image recorder and for the supply thereof with electrical power, and for signal transmission from the at least one electronic image recorder to an external evaluation and display apparatus for evaluating and displaying the recorded image signals. The cable may also comprise parts extending next to one another which are mechanically separated from one another. The cable is preferably embodied as a ribbon cable or as a flexible circuit board.

According to the invention, the endoscope or exoscope comprises an optical unit rotatable about a first axis of rotation, which optical unit comprises the at least one electronic image recorder, which is therefore mounted in a manner rotatable about the first axis of rotation. The axis of rotation is identical or approximately parallel to the direction of view of the endoscope or exoscope. The cable is connected to the optical unit and can be wound, at least over a restricted angle range, on a circumferential surface of the optical unit. In particular, the optical unit also comprises at least one objective, to which the electronic image recorder for recording an image of the object field is assigned, and optionally further mechanical, optical and/or electronic components. By way of example, the direction of view can be defined by the optical axis of the at least one objective. In particular, the circumferential surface of the optical unit can be a cylindrical barrel surface, within which the electronic image recorder and the objective and optionally further components are arranged. Furthermore, provision is made according to the invention for the distal end region of the endoscope or exoscope, that is to say in particular the distal end section of the shaft or the head part which is widened in relation to the shaft, to have an inner cavity, in which a cable storage is held, which provides the cable section wound-up in the case of rotation of the optical unit and holds an unwound cable section in the case of a rotation of the optical unit in an opposite direction of rotation.

Here, the distal end of the cable, which is connected to the optical unit, will move with the rotation of the optical unit. In particular, a distal section of the cable is pushed into the cavity during unwinding. Here, the proximal end of the cable in the instrument is mounted fixedly or almost fixedly in the axial direction.

By way of example, the endoscope or exoscope may also be a stereo optical system. By way of example, the at least one electronic image recorder can be a CCD (charge-coupled device). In particular, such a stereo optical system comprises a plurality of objectives, which are spaced apart in a direction across a direction of view of the observation optical system and which each generate an image of the object field on respectively one, or else on a common, assigned electronic image recorder. The objectives and image recorder are arranged within the optical unit. In particular, the objectives are arranged with a fixed spatial relationship to one another, wherein the distance between two objectives measured across the direction of view represents the stereo basis. With the respective optical axes thereof, the objectives are arranged parallel or at an angle with respect to one another, which angle is determined by the stereo basis and the desired working distance. What is possible to achieve by an angled arrangement is that the center of each half image of the stereoscopic image represents the same point of the object field at the preferred working distance. In the case where the optical axes of the objectives are at an angle with respect to one another, the "direction of view" of the endoscope or exoscope denotes a mean direction between the optical axes. By way of example, the optical unit then comprises two image sensors and/or two objectives for generating the stereo image.

Endoscopes and exoscopes comprise distal illumination units for illuminating a location to be observed sufficiently. These illumination units may be distally attached illumination units such as LEDs. Provision can also be made for optical waveguides, in particular with distally connected windows or optical elements, as illumination units.

Since a rotatable optical unit, which comprises the electronic image recorder and wherein the supply and/or signal cable of the electronic image recorder can be wound and unwound on the circumferential surface of said optical unit, and a cavity in the distal end region of the endoscope or exoscope, in which cavity a cable storage is arranged, are provided it becomes possible, in a simple manner, to supply the electronic image recorder mounted in the optical unit in a rotatable manner with electrical power and to transmit signals to and from the electronic image recorder. Here, twisting of the cable is not necessary. Likewise, it is possible to avoid a displacement of the cable within the shaft, which would be connected with wear and tear of the cable and possibly of further components. In particular, the cable can be securely laid within the shaft. At the same time, this ensures that the cable does not adversely affect the use of the endoscope or exoscope and, in particular, that it does not constitute a restriction of the field of view of the endoscope or exoscope, or of the working region of a surgeon during a surgical intervention performed under observation by the endoscope or exoscope. Finally, what can also be achieved in this manner is that the cable is largely protected from dirtying during such a surgical intervention and the endoscope or exoscope can be cleaned and sterilized in a simple manner.

In particular, the design according to the invention can enable, in a permanent manner, a rotation of the optical unit through 180° without damaging the connected cable.

In accordance with a preferred embodiment of the invention, the end region of the endoscope or exoscope comprises a hermetically sealed housing, within which the cavity holding the cable storage is formed. Within the hermetically sealed housing, the optical unit with the at least one electronic image recorder is held and mounted in a rotatable manner. In particular, the hermetically sealed housing can be embodied to withstand autoclaving, as a result of which particularly simple cleaning and sterilizing of the endoscope or exoscope is made possible. As a result of the embodiment according to the invention, it is possible to achieve a particular advantages that, when passing through the hermetically sealed housing, for example from a head part to the shaft of the endoscope or exoscope, the cable does not perform a displacement or any other movement during a rotation of the optical unit, and so a hermetically sealed passage of the cable through the housing is achievable in a simple manner.

Preferably, the first axis of rotation is directed substantially perpendicular to a longitudinal axis of the shaft. In a particularly advantageous manner, the endoscope or exoscope is embodied with a 90° optical system, i.e. a direction of view of the endoscope or exoscope is at an angle of approximately 90° in relation to the longitudinal axis of the shaft; in this case, the first axis of rotation is parallel to the direction of view of the endoscope or exoscope. Particularly in the case of an exoscope, such a design enables an observation of an operation field without substantially restricting the work space of the surgeon and enables a holder having a comparatively simple design.

In accordance with a preferred embodiment of the invention, the first axis of rotation is substantially perpendicular to the longitudinal axis of the shaft, and the winding and unwinding of the cable onto and from the optical unit, respectively, is performed in a substantially tangential direction which is substantially parallel to the longitudinal axis of the shaft. What this achieves is that the holder for an unwound cable section or the supply of a cable section to be wound-up are in the direction of the shaft, and so the cable storage may likewise be arranged substantially in the shaft direction, as seen from the optical unit. Furthermore, the cable storage can advantageously be embodied in such a way that it has a greater extent in the longitudinal direction of the shaft than in the transverse direction. This enables a particularly compact and space-saving design.

In accordance with a further preferred embodiment, in a completely unwound state, the cable is connected laterally on the optical unit when viewed in the direction of the longitudinal axis of the shaft.

What is achieved by virtue of the cable not being connected to the optical unit at for instance a proximal location thereof, but rather being connected laterally on the optical unit is that the cable can be placed into the cavity in a defined manner. In particular, said cable is not kinked when the optical unit is rotated, but what happens is that the unwound part of the cable is pushed into the cavity in a defined manner. As a result, the cable is particularly spared and excessive load on, or tiring of, the material is avoided.

In a preferred manner, the cable is placed within the cavity in the form of at least one arc; such an arc may also be referred to as a "bight". The cable section forming the arc is a cable section wound from the circumferential surface of the optical unit when rotating the optical unit in an appropriate direction of rotation, or the cable section adjoining thereto. A length of cable, which corresponds approximately to the length taken up by the arc, is available for winding onto the circumferential surface of the optical unit. Provision can also be made for the cable section to be laid in a meandering form within the cavity, i.e. for more than one arc to be provided, wherein the successive arcs have opposite curvatures. Furthermore, provision may be made for further bends or deflections of the cable, which may be fixed and therefore independent of the rotation of the optical unit. In order to ensure that the cable is placed in the form of at least one arc into the cavity, it may be pre-bent in an elastic manner or itself be embodied as a correspondingly formed spring; by way of example, this can be achieved by an elastomeric coating which is applied in the curved state of a flat ribbon cable or flexible circuit board. As a result of the cable forming at least one arc within the cable storage, receiving or providing a wound-up or unwound cable section without the cable being damaged is possible in a simple manner.

In accordance with a preferred embodiment, the region of the cable in which it forms the at least one arc or the at least one bight is placed freely into the cavity; that is to say, no guide is provided in the curved region of the arc, at best provision is made for a one-sided abutment surface for the approximately straight part of the cable. What can be achieved here by selecting an appropriate stiffness of the cable is that a reproducible and low wear-and-tear reception or provision of a wound-up or unwound cable section is made possible, even without a guide. In this manner, it is possible to produce a low friction and low wear-and-tear cable connection to the rotatable optical unit.

Preferably, the at least one arc maintains its direction of curvature when rotating the optical unit and therefore when winding and unwinding. All that changes when the cable is pushed into the cavity or pulled therefrom again by the rotation is the radius of the arc, the number of arcs or the arrangement of the arcs. In particular, when the direction of rotation is changed, the cable is not repeatedly exposed to opposing curvatures or kinks, which would lead to material fatigue at the bent location. As a result, the cable is routed in the cavity in a defined manner.

In accordance with a further preferred embodiment, the cable section unwound by the circumferential surface of the optical unit or the cable section to be wound thereon is routed by at least one reel arranged in the cavity. Said reel is preferably embodied to be rotatable about a second axis of rotation, wherein the second axis of rotation is, in particular, substantially parallel to the first axis of rotation and therefore preferably perpendicular to the longitudinal axis of the shaft. This enables holding and provision of the cable section which is particularly secure and insensitive to changes in position and tremors of the endoscope or exoscope. The at least one reel can also be embodied in a stationary manner, i.e. as a non-rotatable deflection. The cable is routed over the outer surface of the reel. Therefore, the reel is situated, in particular, at the location of the cable where the latter forms an arc.

In a further embodiment of the invention, the at least one reel is formed by an illumination unit.

As a result of the reel being formed by an illumination unit, the cable routing according to the invention is possible in a particularly space-saving manner since an already present element assumes the function of the reel.

Preferably the at least one reel, over which the cable section is routed, is mounted in a displaceable manner. In particular, the reel is mounted in such a way that it is displaceable in a direction substantially parallel to the longitudinal direction of the shaft. What this renders possible is that the cable is always routed by the reel, also in the not completely wound or unwound state. As a result, further improved safety of the provision and holding of this cable section is achievable.

In a particularly advantageous manner, the at least one reel, over which the cable is routed, is displaceable in a spring-loaded manner. What can be achieved by the spring load on the displacement of the reel is that the cable is always under tension, as a result of which further improved safety when routing the cable by the reel is achievable. By way of example, the tension force exerted by the spring load of the reel and acting tangentially on the optical unit can be compensated for by a counteracting spring in the mount of the optical unit or in a drive of the optical unit.

In accordance with a further preferred embodiment, the cable within the cavity is routed over two reels, which are mounted on a two-armed lever, which is swivelable about a third axis, wherein the third axis is substantially parallel to the axis of rotation of the optical unit. In particular, a spring load can be placed on the two-armed lever in such a way that the cable always securely rests against the two reels. As a result of the cable being routed on two reels which are mounted on a two-armed lever, it is possible to achieve a low friction and secure repositioning of the reels and therefore a particularly secure routing of the cable.

In accordance with a preferred embodiment, the cable storage is embodied in the form of two layers arranged one above the other in the direction of the first axis of rotation, with a part of the cable or else a further flexible element, such as a wire, that is likewise wound and unwound on the optical unit, being respectively held in said layers. Here, sections of the cable or the flexible element held in the first and second layer are wound onto the optical unit in opposite directions. When the cable, or the part of the cable held in the first layer, is wound by rotating the optical unit in a given direction, the part of the cable held in the second layer or the flexible element held therein is therefore simultaneously unwound from the circumferential surface of the optical unit, and vice versa. Furthermore, the first and the second layer within the cavity are, in the process, laid or routed in opposite directions, in particular laid or routed in a mirror-inverted manner. An advantage that can be achieved by this is that a tension force exerted by a spring of a reel in the first layer is compensated for by an opposite or mirror-inverted tension force in the second layer such that, overall, a reduced, or no, torque is exerted on the optical unit. The same applies to possible elastic forces, which are generated by bending the cable and which likewise may lead to a torque acting on the optical unit.

It is understood that the features mentioned above and still to be explained below can be used not only in the respectively specified combination, but also in other combinations or on their own, without departing from the scope of the present invention.

BRIEF DESCRIPTION OF THE DRAWINGS

Further aspects of the invention emerge from the following description of a preferred exemplary embodiment and from the attached drawing. In detail.

DETAILED DESCRIPTION OF THE INVENTION

In the following text, the invention is explained on the basis of an embodiment which is embodied as an exoscope.

Figure 1A:
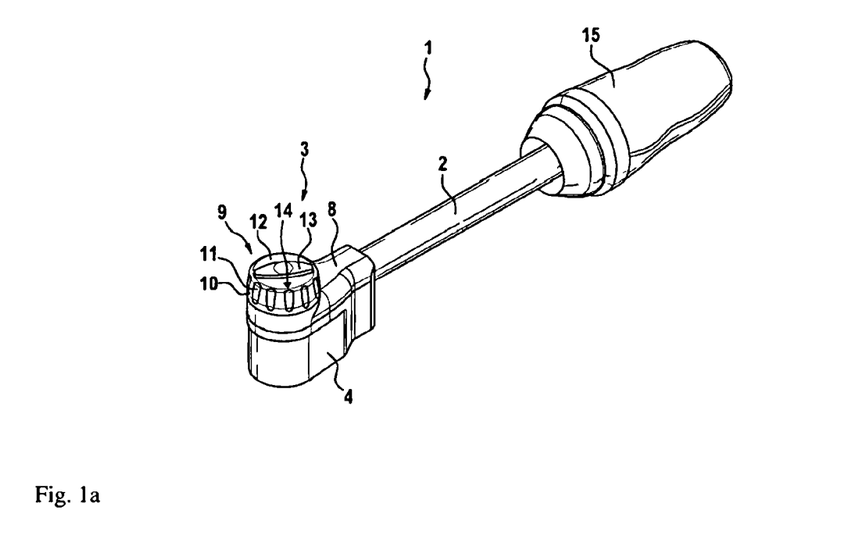
FIGS. 1a and 1b show an exemplary embodiment of an exoscope according to the invention in two different perspective views.
Figure 1B:
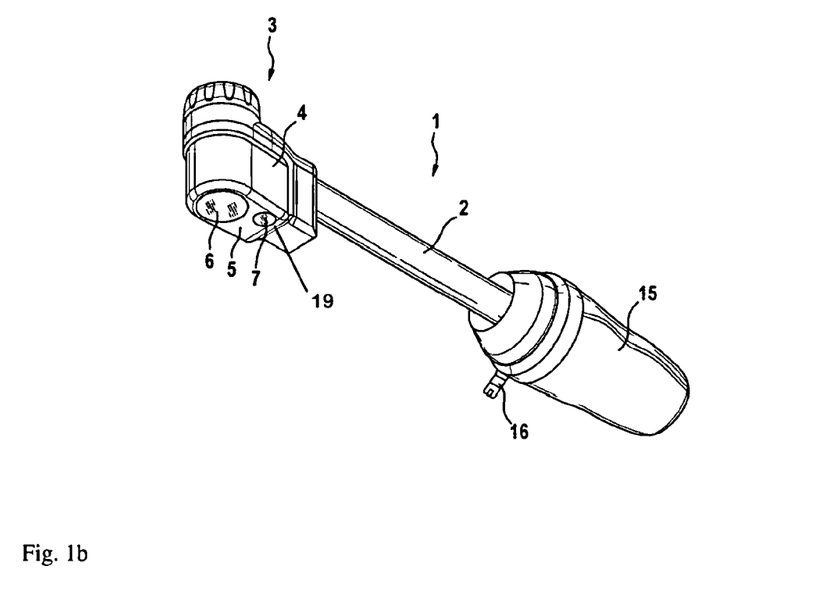

FIGS. 1a and 1b show such an exoscope 1 in two different perspective views. The exoscope 1 comprises an elongate cylindrical shaft 2, at the distal end of which a head part 3, which is widened compared to the shaft, is arranged. The head part 3 comprises a housing 4, the distal region of which has an approximately semi-cylindrical form, wherein the axis of the semi cylinder is at an angle of approximately 90° with respect to the longitudinal axis of the shaft 2. An observation window 6, through which an observation optical system arranged in the interior of the housing 4 receives light from an object field, is inserted into a base surface 5 of the housing. The base surface 5 furthermore comprises an illumination window 7, behind or in which an illumination unit 19 terminates and through which illumination light can be emitted for illuminating the object field. By way of example, the illumination unit can be a light source arranged behind the illumination window 7 in the interior of the head part. However, optical waveguides may also terminate in the region of the illumination window 7 or the end surfaces of the optical waveguides themselves may form the illumination window 7, wherein the optical waveguides are routed through the shaft 2 and transmit light from the light source arranged outside of the head part 3. The observation window 6 is preferably a plane parallel plate, while the illumination window 7 is preferably embodied as a convex lens.

A rotary cap 9 is placed on a distal end region of a cover surface 8 lying opposite the base surface 5, which rotary cap 9 comprises a plurality of grip depressions 11 on the circumferential side 10 thereof and supports a rotary grip 13 on the upper side 12 thereof. Furthermore, the rotary cap 9 comprises a marking 14, which makes it easy to identify the rotary position of the rotary cap 9. The exoscope 1 furthermore comprises a handle 15, which has a connector 16 for connecting signal and supply cables. By way of example, the handle 15 may also contain a cooling apparatus or a light source for generating illumination light, which is guided to the illumination window 7 through optical waveguides.

Figure 2:
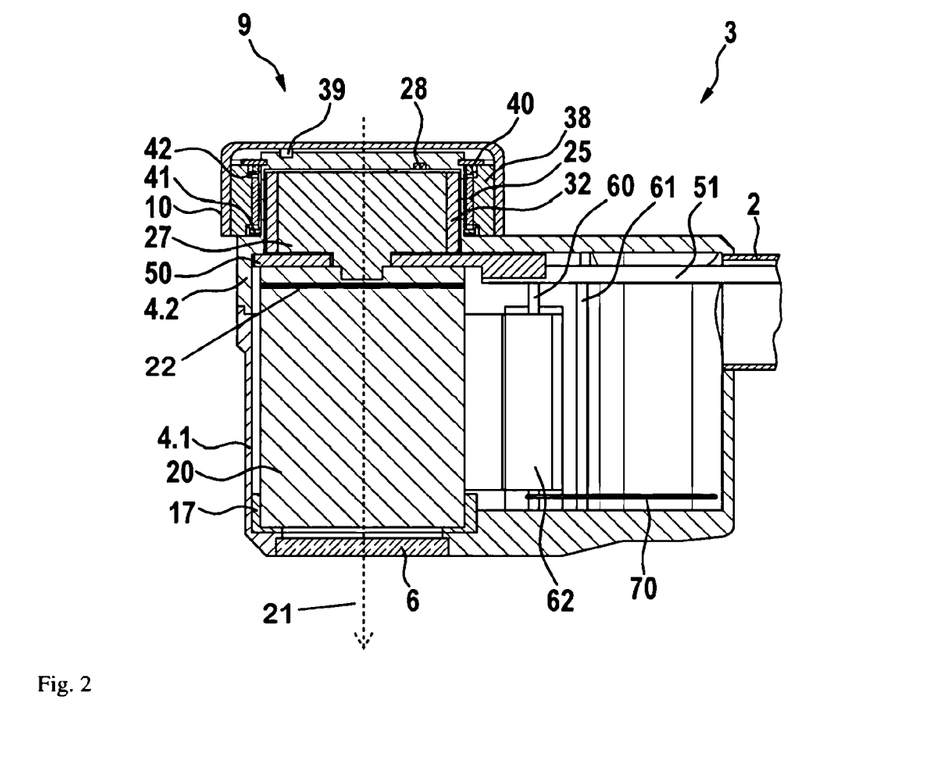
FIG. 2 shows a perpendicular longitudinal section through the head part of the exoscope depicted in FIGS. 1a and 1b.

As shown in the sectional illustration of FIG. 2, the housing 4 is composed of a housing lower part 4.1 and a housing upper part 4.2, which are connected to one another in a hermetically sealed manner, for example by welding. The observation window 6 is inserted in a hermetically sealed manner into the base surface 5 formed by the housing lower part 4.1, for example by soldering, just like the illumination window 7 not depicted in FIG. 2 (see FIG. 1b). Therefore, the housing 4 is, overall, terminated with a hermetic seal or connected to the shaft 2 of the exoscope in a hermetically sealed manner, which shaft is hermetically sealed in the proximal region thereof. Arranged within the interior of the housing 4 is an optical unit 20, which comprises at least one objective with an associated electronic image recorder 22 and optionally further optical and electronic components (not depicted here). The objective defines a direction of view 21 of the exoscope which, in the depicted example, extends perpendicular to the window 6 and to the longitudinal axis of the shaft 2.

Within the housing 4, the optical unit 20 is mounted in a rotatable manner by means of a sliding bearing 17 and is manually adjustable from outside of the housing by means of a magnetic drive using a rotary cap 9, which is placed on the side of the head part 3 opposite to the observation window 6. To this end, the magnetic drive comprises first magnets 25, which are fastened to the inner side of a ring-shaped first magnet support 38, which is connected to the rotary cap 9 for rotation therewith, and second magnets 32, which are held on the barrel surface of a cylindrical second magnet support 27 connected to the optical unit 20 for rotation therewith. The first and the second magnets 25, 32 are arranged in such a way that they interact through a wall of the housing upper part 4.2 for transmitting a torque from the first magnet support 38 to the second magnet support 27. The rotary cap 9 with the first magnet support 38 is rotatable about the same axis of rotation as the optical unit 20 with the second magnet support 27. Therefore, rotating the rotary cap 9 can cause a corresponding rotation of the optical unit. The possible adjustment angle of the rotary cap 9 is restricted by a stop 39, while the angle of rotation of the optical unit 20 is restricted by a stop 28. In addition to restricting the angles, this also ensures ideal coupling between the magnetic coupling elements. In general, a range of ±90° is sufficient as an adjustment angle range. Slide sealing rings 41, 42 are provided for sealing the rotary cap 9. The optical unit 20 is embodied with a substantially cylindrical barrel or circumferential surface, wherein the axis of rotation 18 corresponds to the cylinder axis and the direction of view 21 (see FIG. 4a).

FIG. 2 shows exemplary measures for dissipating heat. On the side opposite to the sliding bearing 17, the optical unit 20 is in contact with thermal conduction sheets 50 made of graphite, by means of which thermal losses generated in the optical unit 20 are conducted along a heat pipe 51, as a result of which the thermal losses are dissipated through the shaft 2 into the proximal end region of the exoscope 1 or into the handle 15. Furthermore, FIG. 4 schematically shows a routing of connection lines to the optical unit 20. To this end, reels in the form of deflections 61, 62 are provided, by means of which a cable 62, which may for example be embodied as a flat ribbon cable or as a flexible circuit board, is routed. A guide 70 is provided for displacing the deflection 60. The cable storage formed hereby, which provides the section of the cable 62 to be wound onto the circumferential surface of the optical unit 20 when the optical unit 20 is rotated or which holds the unwound section in the case of an opposite rotation, is explained in more detail in the following text.

Figure 3:
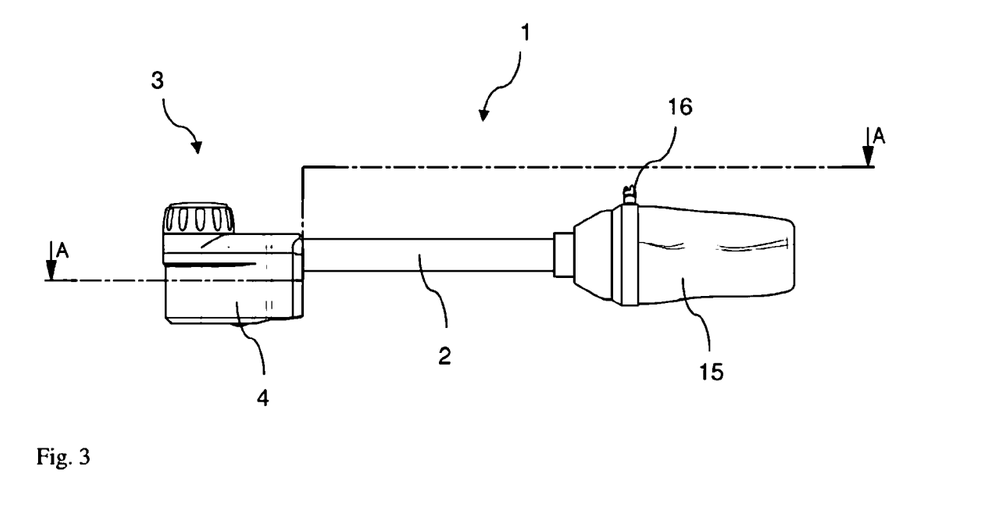
FIG. 3 shows a side view of the exoscope depicted in FIGS. 1a and 1b.

FIG. 3 shows a side view of the exoscope 1 described above, in respect of which reference is made to the description in relation to FIGS. 1a and 1b. The section line A-A is plotted in FIG. 3, along which the horizontal longitudinal section through the head part depicted in FIGS. 4a to 4c is cut.

Figure 4A:
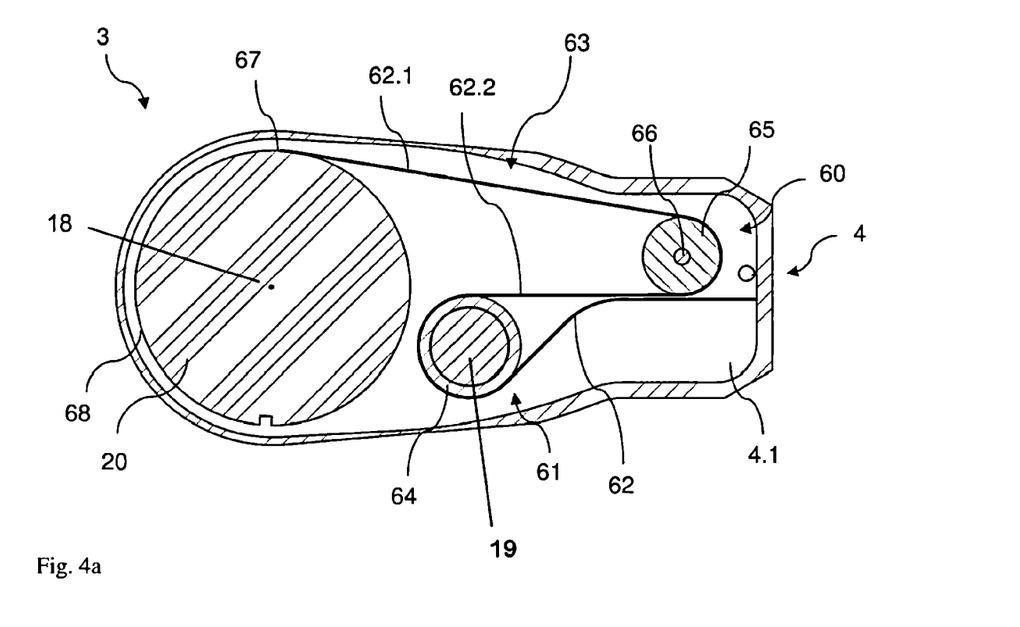
FIGS. 4a to 4c show a horizontal longitudinal section through the head part of the exoscope depicted in FIGS. 1a and 1b in three different rotational positions of the optical unit comprising a cable storage in accordance with a first embodiment.
Figure 4B:
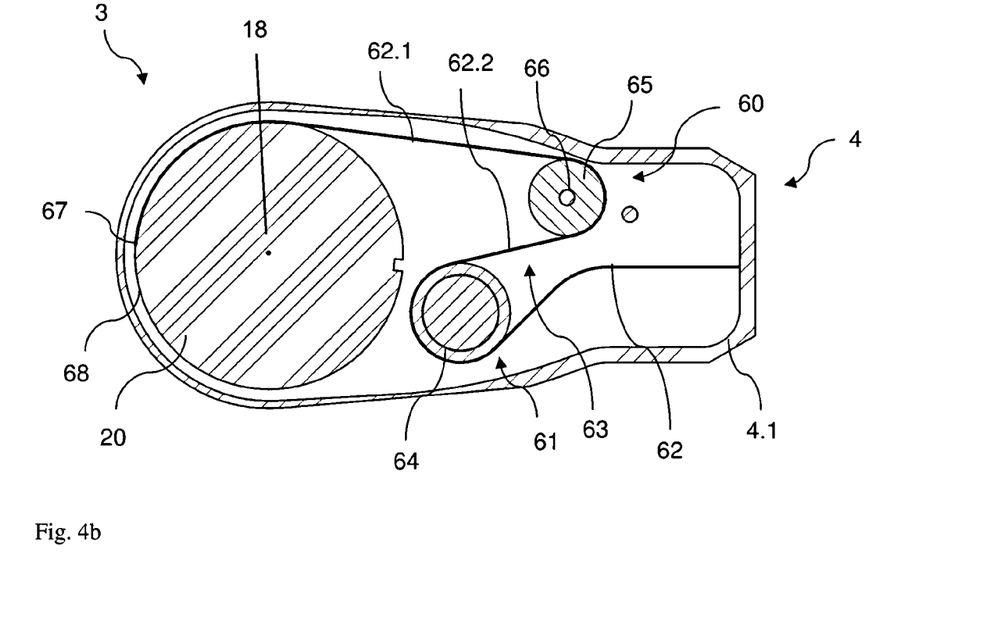
Figure 4C:
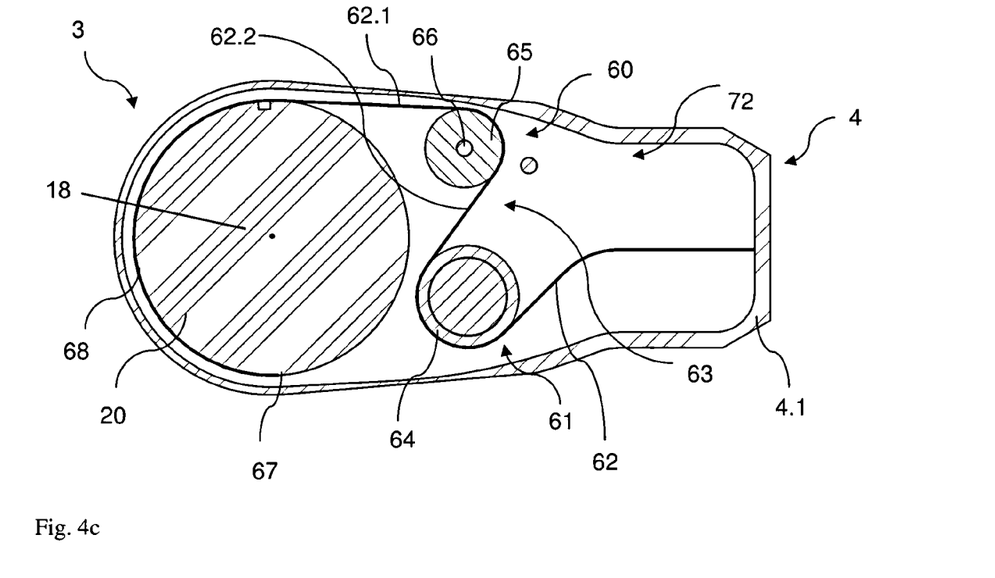

FIGS. 4a to 4c respectively show the cable storage in accordance with a first embodiment in a horizontal longitudinal section in different rotational positions of the optical unit 20, which is mounted in a rotatable manner about the axis of rotation 18, wherein FIGS. 4a and 4c show the end positions corresponding to rotation through approximately 180° and FIG. 4b shows a rotational position lying therebetween. The rotation angle of the optical unit 20 is restricted by one or more stops.

What can be seen in FIG. 4a is that the substantially cylindrically formed optical unit 20 and the cable storage 63, which comprises a section of the cable 62 and the deflections 60, 61 serving as reels, are held within the hermetically sealed housing 4, the housing lower part 4.1 of which is cut in FIG. 4a. The deflection 61 comprises a stationary cylinder 64, which is securely held in the housing 4. The stationary cylinder 64 contains an illumination unit 19, for example in the form of a distal end section of the optical waveguides for illuminating the object field, as a result of which a particularly space-saving design is made possible. The further deflection 60 comprises a cylindrical reel 65, which is mounted in a manner rotatable about an axis of rotation 66. In the rotational position of the substantially cylindrically designed optical unit 20, shown in FIG. 4a, the cable joins the circumferential surface 68 of the optical unit at a connection point 67, from where it is routed into the interior of the optical unit for connection to the electronic image recorder and, optionally, further electronic components; however, it is not wound onto the circumferential surface 68 of the optical unit. Accordingly, the cable storage holds a relatively large section of the cable, for the purposes of which the deflection 60 is arranged in a proximal end position. In this completely unwound state of the cable, the connection point 67 thereof on the optical unit 20 is situated laterally on the optical unit 20 when viewed in the longitudinal direction of the shaft, i.e. as depicted along the section A-A in FIG. 3.

In the rotational position of the optical unit 20 shown in FIG. 4b, the cable 62 is wound onto the circumferential surface 68 of the optical unit over an angle range of approximately 90°. Therefore, the cable storage 63 is required still to hold a shorter section of the cable 62. Accordingly, the deflection 60 is in a central position, as depicted schematically in FIG. 4b.

In the situation shown in FIG. 4c, the cable 62 is wound onto a region comprising approximately 180° of the circumferential surface 68 of the optical unit 20. In this situation, the cable storage 63 has practically completely provided the available section of the cable 62 and only still comprises a minimum section of the cable 62, which is required for maintaining secure routing. The length of cable wound up and to be provided by the cable storage 63, which is once again to be held by the cable storage 63 during unwinding, is approximately 55 mm in the case of where the cylindrical circumferential surface has a diameter of e.g. 35 mm.

No deflections 60, 61 are provided in an alternative embodiment (not depicted here). Instead, the cable is routed freely in the cavity. The profile of the cable then corresponds to the one in FIGS. 4a-4c. In this case, the cable is laid in two arcs, the radius and position of which change when the optical unit is rotated, but the direction of curvature of which remains unchanged. This avoids alternate bending or kinking of the cable.

Figure 5:
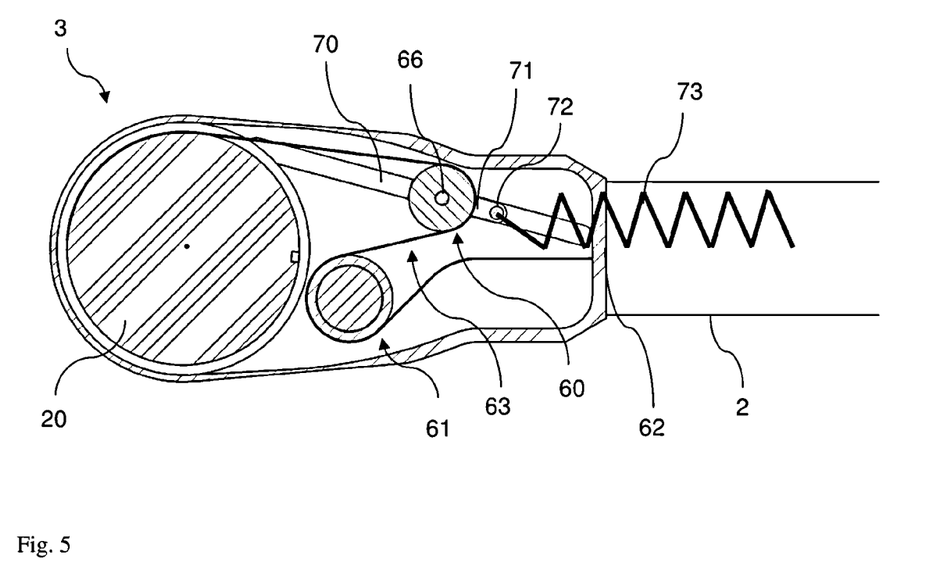
FIG. 5 shows a longitudinal section in accordance with FIGS. 4a to 4c with additional details.

The displacement of the axis 66 of the deflection reel 65, indicated in FIGS. 4a to 4c, occurs along a linear guide 70, which is schematically depicted in FIG. 5. The axis of rotation 66 is connected to an extension 71, which is guided in a displaceable manner in the guide 70. The extension 71 supports a pin 72, on which a spring 73, which is indicated in FIG. 5, is attached. Here, the illustration in FIG. 5 is only to be taken symbolically; the spring 73 is likewise arranged within the hermetically sealed housing 4 and, for example, engages on an inner side of the housing 4 such that the axis of rotation 66 is loaded for tensioning the cable 62.

Proceeding from the connection point 67, the cable 62 is routed along a first free path 62.1 to the deflection reel 65, from the latter along a second free path 62.2 to the deflection cylinder 64 and from there it is routed on in a stationary manner. When rotating the optical unit 20 counterclockwise, the cable 62 is wound onto the circumferential surface 68, wherein the deflection reel 65 follows such that an appropriate length of cable is provided. When rotating the optical unit 20 clockwise, the cable 62 is unwound, wherein the deflection reel 65 is withdrawn by the spring 73 such that the unwound cable length is held. The cable 62 is always kept under tension by the spring force of the spring 73 and therefore securely routed via the deflections 60, 61. A curvature of the cable 62 with an inadmissibly small radius of curvature, and hence kinking of the cable 62, can be reliably avoided hereby. After passing through the housing 4, the cable 62 extends within the shaft 2 of the exoscope to the handle 15 and is routed there to the connector 16, where an external supply, evaluation and display apparatus can be connected (see FIG. 3). The passage of the cable 62 through the housing 4, which is not exposed to the movement of the cable 62 and can therefore easily be embodied in a hermetically sealed manner, is not depicted in the figures.

Figure 6:
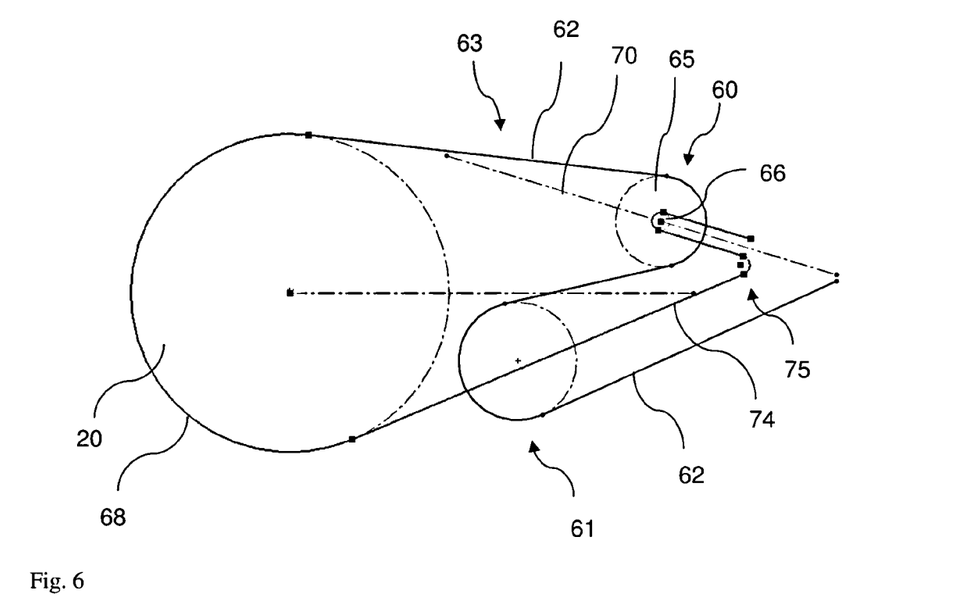
FIG. 6 shows a schematic illustration of a second embodiment of a cable storage.

A second embodiment of a cable storage is shown in FIG. 6 in a schematic illustration. As explained in relation to the first exemplary embodiment, the cable 62, proceeding from the optical unit 20, is routed via a first deflection 60, which comprises a reel 65 rotatable about an axis of rotation 66, and a stationary second deflection 61, wherein the rotatable reel 65 is guided in a linearly displaceable manner and loaded by a spring for tensioning the cable 62 and for repositioning the reel 65. In a layer mounted thereabove, a flexible element, for example an elastically flexible wire 74, which can be wound onto the circumferential surface 68 of the optical unit 20 or wound therefrom in the opposite direction, is likewise routed over two deflections. A first deflection 75 of the wire 74 has a stationary embodiment, while a second deflection is brought about by means of a rotatable reel which is mounted in a rotatable manner on the axis of rotation 66 of the first deflection 60 of the cable; the radii of curvature of the deflections of the wire 74 may be different, in particular smaller, than those of the deflections of the cable 62 due to the elastic properties of the wire 74. The wire 74 is routed about the second deflection in such a way that the arc of the wire 74 formed thereby has an opposite direction to the arc formed by the first deflection 60 of the cable 62. Therefore, the wire 74 is likewise kept under tension by the spring attached to the axis of rotation 66, as a result of which a force is exerted on the wire 74 which is substantially equal to the force exerted on the cable 62.

Since the cable 62 and the wire 74 are attached to the optical unit 20 in opposite directions, the torque exerted from the cable 62 on the optical unit 20 is compensated for by the wire 74.

Figure 7:
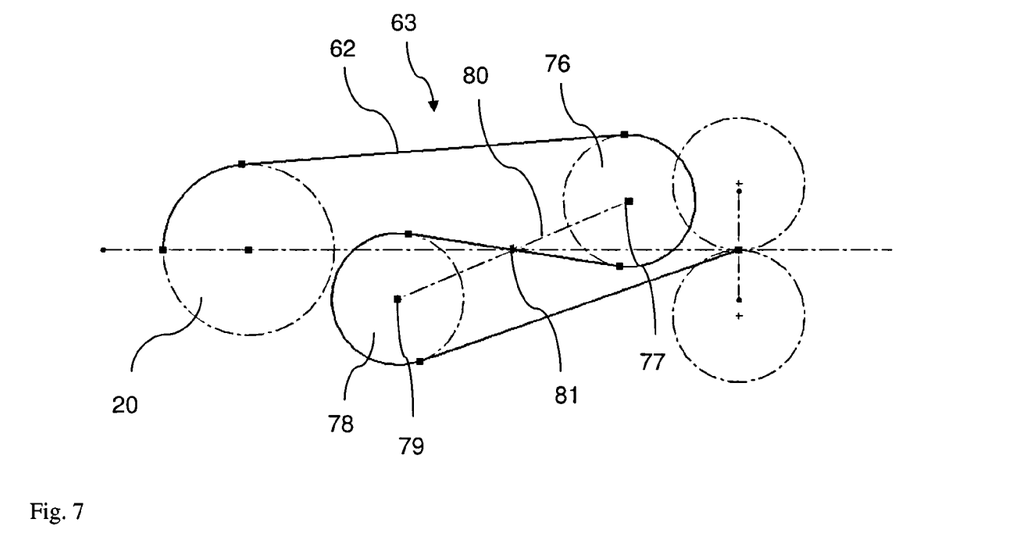
FIG. 7 shows a schematic illustration of a third embodiment of a cable storage.

A third embodiment of a cable storage is depicted schematically in FIG. 7. Here, the cable 62, proceeding from the optical unit 20, is routed over a first rotatable reel 76 with an axis of rotation 77 and a second rotatable reel 78 with an axis of rotation 79. The first and second rotatable reels 76, 78 are mounted in a frame with the axes of rotation 77, 79 thereof, which frame is embodied as a two-armed lever 80 with an axis of rotation 81. The axes of rotation 77, 79 of the reels 76, 78 and the axis of rotation 81 of the lever 80 are substantially parallel to one another. The lever 80 is pretensioned in a clockwise direction by a spring (not depicted here). If, proceeding from the situation shown in FIG. 7, the cable is wound further onto the circumferential surface 68 by rotating the optical unit 20 counterclockwise, the lever 80 likewise rotates counterclockwise, as a result of which the length of the cable 62 held in the cable storage 63 is shortened and a cable section is provided for winding onto the circumferential surface 68 of the optical unit 20. Accordingly, the unwound cable section in the case of a clockwise rotation of the optical unit 20 is held in the cable storage 63 by a clockwise rotation of the lever. No torque is likewise exerted on the optical unit if a further flexible element, which may be a further part of the cable or e.g. a wire, is routed over a mirror inverted arrangement in a layer mounted over the arrangement shown in FIG. 7 along the axis of rotation 81.

For reasons of clarity, not all reference signs are depicted in all figures. Reference signs explained in relation to one figure have the same meaning as in the remaining figures.

The invention claimed is:

1. An endoscope or exoscope, comprising:
a shaft;
at least one objective arranged in a distal end region of the endoscope or exoscope;
at least one electronic image recorder arranged in the distal end region of the endoscope or exoscope and configured to record an image of an object field; and
a cable, routed within the endoscope or exoscope, configured to supply and/or transmit an image from the electronic image recorder;
wherein the distal end region of the endoscope or exoscope includes a housing;
wherein the electronic image recorder includes an optical unit within the housing, which is rotatable relative to the housing about a first axis of rotation parallel to a direction of view of the endoscope or exoscope, and on which the cable is connected and configured to be wound on a circumferential surface of the optical unit;
wherein the distal end region of the endoscope or exoscope includes a cavity, in which a cable storage is provided, the cable storage configured to hold a cable section of the cable which is wound onto the circumferential surface of the optical unit when rotating the optical unit in a first direction about the first axis of rotation and unwound from the circumferential surface of the optical unit when rotating the optical unit in a second direction about the first axis of rotation, the second direction opposite the first direction;
wherein the first axis of rotation is directed perpendicular to a longitudinal axis of the shaft;
wherein the cable section of the cable in the cable storage forms at least one arc; and
wherein, in a region of the at least one arc, the cable is routed by at least one reel arranged in the cavity.

2. The endoscope or exoscope according to claim 1, wherein the housing is a hermetically sealed housing; and
wherein the cable storage is held in the hermetically sealed housing.

3. The endoscope or exoscope according to claim 1, wherein the cable is configured to be wound onto the circumferential surface of the optical unit, or unwound therefrom, in a tangential direction relative to the circumferential surface, which is directed parallel to the longitudinal axis of the shaft.

4. The endoscope or exoscope according to claim 1, wherein, in a completely unwound state, the cable is connected laterally on the optical unit when viewed in a direction of the longitudinal axis of the shaft.

5. The endoscope or exoscope according to claim 1, wherein the cable section forming the at least one arc is placed freely into the cavity.

6. The endoscope or exoscope according to claim 1, wherein the at least one arc maintains a direction of curvature thereof when winding and unwinding the cable.

7. The endoscope or exoscope according to claim 1, wherein the at least one reel is formed by an illumination unit.

8. The endoscope or exoscope according to claim 1, wherein the at least one reel is mounted in a displaceable manner.

9. The endoscope or exoscope according to claim 8, wherein the at least one reel is mounted in a spring-loaded displaceable manner.

10. The endoscope or exoscope according to claim 1, wherein the cable section is routed by at least two reels arranged in the cavity, the at least two reels mounted on a two-armed swivelable lever.

11. The endoscope or exoscope according to claim 1, wherein the cable storage includes two layers lying above one another in a direction of the first axis of rotation;
wherein at least one part of the cable is held in a first layer and a further part of the cable or a flexible element is held in a second layer; and
wherein the part of the cable held in the second layer or the flexible element held in the second layer configured to be wound or unwound in an opposite direction on the circumferential surface of the optical unit compared to the part of the cable held in the first layer and routed in the opposite direction in the cable storage.

12. The endoscope or exoscope according to claim 1, wherein the cable is a first cable; and
wherein the endoscope or exoscope further comprises a second cable, routed within the endoscope or exoscope, configured to supply and/or transmit an image from the electronic image recorder, and configured to be wound on the circumferential surface of the optical unit.

13. The endoscope or exoscope according to claim 1, wherein the at least one reel is displaceable in a direction parallel to the longitudinal axis of the shaft.

* * * * *